US006641537B2

(12) United States Patent
Morris et al.

(10) Patent No.: US 6,641,537 B2
(45) Date of Patent: Nov. 4, 2003

(54) MULTI-ZONE TRANSMITTER FOR QUANTITATIVE ULTRASOUND AND IMAGE MEASUREMENT

(75) Inventors: Richard Franklin Morris, Stoughton, WI (US); Steven Taylor Morris, Madison, WI (US); Duane Anthony Kaufman, Hollandale, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 111 days.

(21) Appl. No.: 09/910,326

(22) Filed: Jul. 20, 2001

(65) Prior Publication Data

US 2003/0018263 A1 Jan. 23, 2003

(51) Int. Cl.⁷ .............................................. A61B 8/02
(52) U.S. Cl. ....................... 600/449; 600/442; 600/448; 128/915; 128/916
(58) Field of Search ................................ 600/473–472; 128/915, 916

(56) References Cited

U.S. PATENT DOCUMENTS

| 3,847,141 A | * 11/1974 | Hoop ........................ 600/437 |
| 4,206,763 A | * 6/1980 | Pedersen ..................... 600/445 |
| 4,509,368 A | * 4/1985 | Whiting et al. ................ 73/624 |
| 4,541,436 A | * 9/1985 | Hassler et al. ............... 600/443 |
| 4,930,511 A | 6/1990 | Rossman et al. |
| 5,348,009 A | * 9/1994 | Ohtomo et al. ............. 600/407 |
| 5,627,567 A | * 5/1997 | Davidson ..................... 345/173 |
| 5,709,206 A | * 1/1998 | Teboul ........................ 600/437 |
| 5,895,357 A | * 4/1999 | Ohtomo ....................... 600/449 |
| 6,027,449 A | * 2/2000 | Mazess et al. .............. 600/449 |
| 6,277,076 B1 | 8/2001 | Morris et al. |
| 6,305,060 B1 | 10/2001 | Morris |

* cited by examiner

Primary Examiner—Francis J. Jaworski
Assistant Examiner—William C. Jung
(74) Attorney, Agent, or Firm—Quarles & Brady LLP

(57) ABSTRACT

An ultrasonic transmission unit for an imaging/quantitative ultrasound device provides for coaxial transducer crystals which may be operated independently with a first crystal operated alone for quantitative measurement and the first and second crystal operated together to provide a broad illumination for imaging of structure.

22 Claims, 3 Drawing Sheets

MULTI-ZONE TRANSMITTER FOR QUANTITATIVE ULTRASOUND AND IMAGE MEASUREMENT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates generally to quantitative ultrasound equipment and in particular, to an ultrasonic transducer providing separate transmission modes for imaging and quantitative measurement.

Quantitative ultrasound may be used to make measurements of in vivo tissue. In one such device used to assess bone quality, in evaluating conditions such as osteoporosis, an opposed ultrasonic transmitter and ultrasonic receiver are positioned across a body member containing trabecular bone. The heel is often the site of measurement because of its ready accessibility, the relatively thin layers of soft tissue surrounding it, and because the heel bone or os calcis is in significant proportion trabecular bone.

The ultrasonic signal after passing through the bone and soft tissue is analyzed to assess bone health. The analysis may determine changes in sound speed, attenuation, or other parameters. One such system is described in U.S. Pat. No. 6,027,449, entitled: "Ultrasonometer Employing Distensible Membranes". This patent is assigned to the assignee of the present case and is hereby incorporated by reference.

While the earliest quantitative ultrasound devices for bone measurement were limited to providing quantitative output, it was recognized that the ability to provide an image could be useful in positioning the body member and therefore in obtaining reproducible results in measurements separated over time. Ultrasonic images may be obtained by scanning a single receiving transducer or by dividing an ultrasonic receiver into a number of elements arranged in an array and separately detecting the received ultrasonic signal at each element. The present invention to be described below is applicable to both techniques.

The separate measurements are analyzed as to speed of sound, or attenuation or another parameter and these analyzed values are mapped to a gray scale and used to produce an image with each gray scale value placed in a picture location (pixel) corresponding to the point of detection of the original ultrasonic signal. The image may be displayed and/or used in an automatic method for identifying a region of interest for quantitative measurement.

BRIEF SUMMARY OF THE INVENTION

The present inventors have recognized that multi-path interference from ultrasound coming around the bone compromises the quantitative analysis of the ultrasound waves coming through the bone. This "around-the-bone" component increases with the larger sized ultrasonic transmitter necessary to fully "illuminate" the bone for imaging purposes.

Once the interference reaches the ultrasonic receiver, it is difficult to remove or compensate for its influence. Accordingly, the present invention provides a dual mode ultrasonic transmitter that provides first, small-area, ultrasonic transmitter which produces a localized source of ultrasonic energy for quantitative measurements, and second a larger ultrasonic transducer, used in conjunction with the smaller ultrasonic transducer which produces a large area ultrasonic wave suitable for imaging the bone and the surrounding tissue. These two modes are used as required.

Specifically then, the present invention provides an imaging/quantitative ultrasonic device having an ultrasonic receiver unit providing a reception aperture of a first predetermined area and an ultrasonic transmission unit having a transmission aperture of a second predetermined area, the ultrasonic transmission unit positioned in opposition across a measurement region from the ultrasonic receiver unit for directing ultrasonic acoustic waves to the reception aperture. The ultrasonic transmission unit further includes a means for independently transmitting ultrasonic acoustic waves from a first and second portion of the transmission aperture. A controller communicates with the ultrasonic transmission unit to alternately transmit ultrasonic waves from (a) only the first of the transmission aperture for preparing a quantitative measurement, and (b) both the first and second portions of the transmission aperture for preparing an image.

In this way, scattered ultrasound coming around the bone may be minimized in the quantitative measurement while still providing a uniform broad area ultrasonic signal for imaging purposes.

The ultrasonic transmission unit may have an electrically separate circular transducer and a coaxially annular transducer.

Thus, the present invention is well adapted to use of standard ceramic transducer technologies.

The first transducer may have a diameter of substantially one inch.

In this way, the transducer can be constructed to match the existing ultrasonic densitometry equipment and provide consistent measurement with other machines.

The ultrasonic receiver may include an array of receiving elements and the controller may communicate with the receiver unit to sequentially (a) detect ultrasonic acoustic waves from only a first portion of the reception aperture when the ultrasonic acoustic waves are being transmitted only from the first portion of the transmission aperture and (b) detect ultrasonic acoustic waves from both the first and the second portion of the reception aperture when the ultrasonic acoustic waves are being transmitted from both the first and second portions of the transmission aperture.

In this way, the receiver can also be used to discriminate between direct and scattered ultrasound.

The ultrasonic transmission unit and ultrasonic receiver unit may be separated by a distance less than twice the diameter of the reception and transmission apertures.

Such a separation ensures that a generally planar acoustic wave may be generated for imaging purposes.

The foregoing features and advantages may not apply to all embodiments of the inventions and are not intended to define the scope of the invention for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
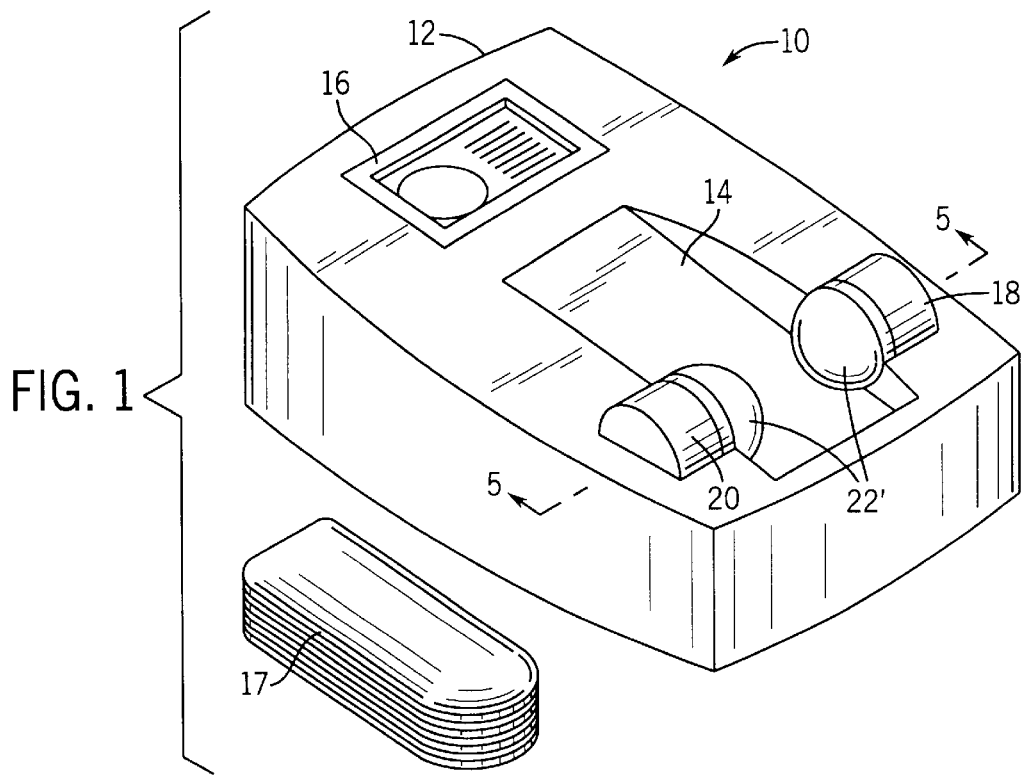
FIG. 1 is a perspective view of an imaging/quantitative ultrasonic densitometer suitable for use with the present invention showing an ultrasonic reception unit and ultrasonic transmission unit opposed across a footwell.

Referring to FIG. 1, an imaging/quantitative ultrasonic device 10 includes a housing 12 having a generally upward opening footwell 14 sized to receive a human foot. At the toe end of the footwell 14 on the upper surface of the housing 12 is a display/touch panel 16 allowing data to be entered into or received from an internal computer (not shown in FIG. 1). Flanking the footwell 14 near the heel end of the footwell is an ultrasonic transmitter unit 18 and an ultrasonic receiver unit 20 supporting at their opposed surfaces compliant bladders 22 holding a coupling fluid such as water. The bladders 22 serve to communicate ultrasonic energy from the contained transducers of the transmitter unit 18 through a patient's foot inserted into the footwell 14 and back out to the contained transducer of the receiver unit 20.

Figure 2:
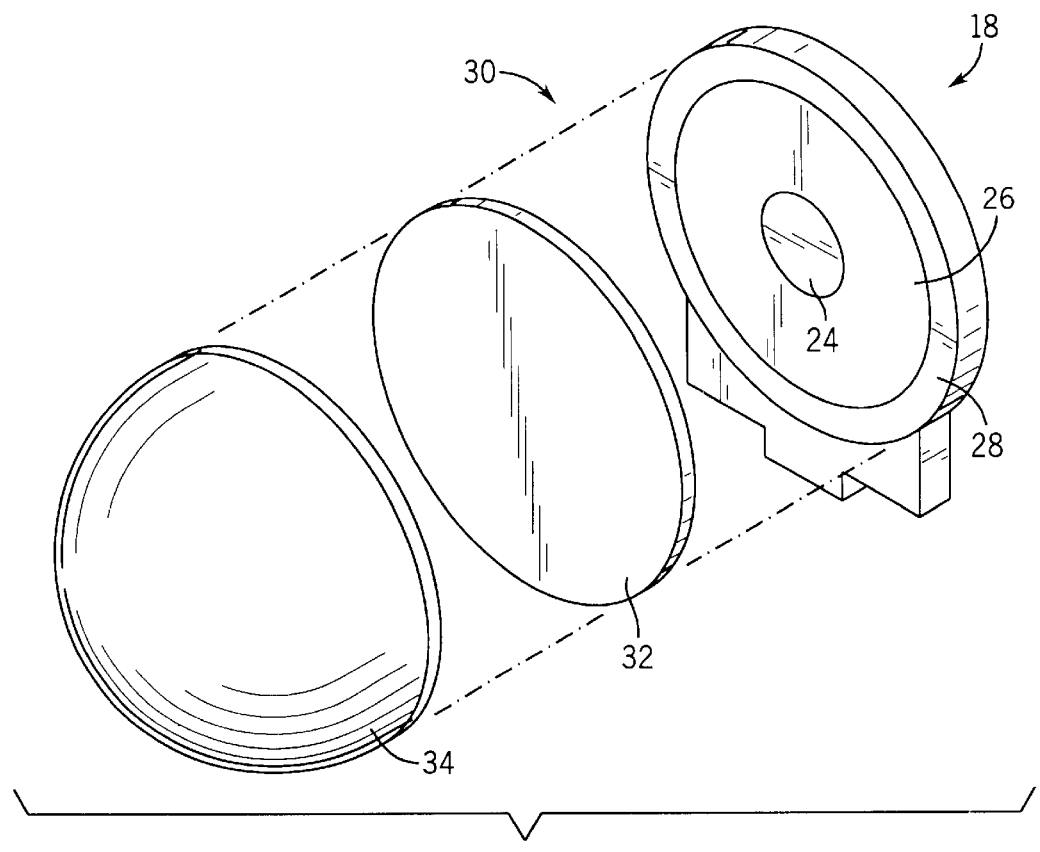
FIG. 2 is an exploded perspective view of the ultrasonic transmission unit of FIG. 1 showing the constituent coaxial transducer, coupling plate and compliant water filled bladder.

Referring now to FIG. 2, the transmitter unit 18 includes a cylindrical, center ultrasonic element 24 coaxially surrounded by an annular, outer ultrasonic element 26, both fabricated of conventional ultrasonic piezoelectric ceramics as is well known in the art. Alternatively, these elements may be made from one piece of ceramic with a dividing kerf and appropriately positioned independent electrodes. The center ultrasonic element 24 may have a diameter of approximately 25 mm whereas the outer annular ring may have a diameter of approximately 90 mm.

The ultrasonic elements 24 and 26 are held in a retaining ring 28 mounted to the side of the footwell as shown in FIG. 1. The retaining ring 28 may include fluid channels for the inflation and deflation of the bladders 34 as is well understood in the art.

A front surface 30 of the ultrasonic elements 24 and 26 are attached to a matching plate 32 providing an impedance coupling between the ultrasonic elements 24 and 26 and water contained within compliant bladder 34. Matching plate 32 may be, for example, a plate of polyester.

Figure 5:
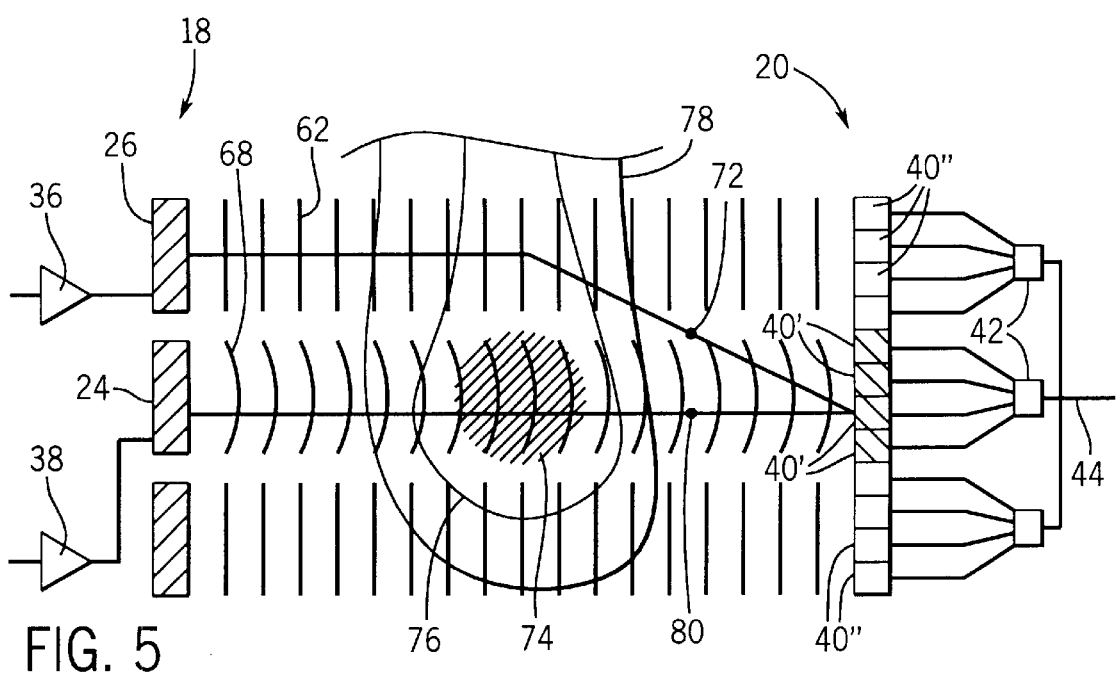
FIG. 5 is a cross-sectional view taken along line 5—5 with a patient's foot in place showing the generation of scatter during the imaging process.

Referring now momentarily to FIG. 5, each of the center ultrasonic element 24 and the outer ultrasonic element 26 include at least one separate electrode to allow them to be independently activated to produce an ultrasonic signal. In one embodiment, the annular, outer ultrasonic element 26 is driven by a separate buffer amplifier 36 from the center ultrasonic element 24, the latter which is driven by buffer amplifier 38. Alternatively, a single buffer amplifier may be used and switched between either the center ultrasonic element 24 alone or the center element 24 plus the outer ultrasonic element 26.

The receiver unit 20 comprises a number of receiving elements 40 generally arrayed over a rectangular grid. Signals from each receiving element are collected by one or more multiplexers 42 to be sent out one or more signal leads 44. The multiplexers 42 are controlled by an external computer signal, as will be described, to allow any individual or combination of receiving element(s) 40 to be read over signal leads 44 to permit scanning over the array of the receiver unit 20 for imaging purposes.

Figure 3:
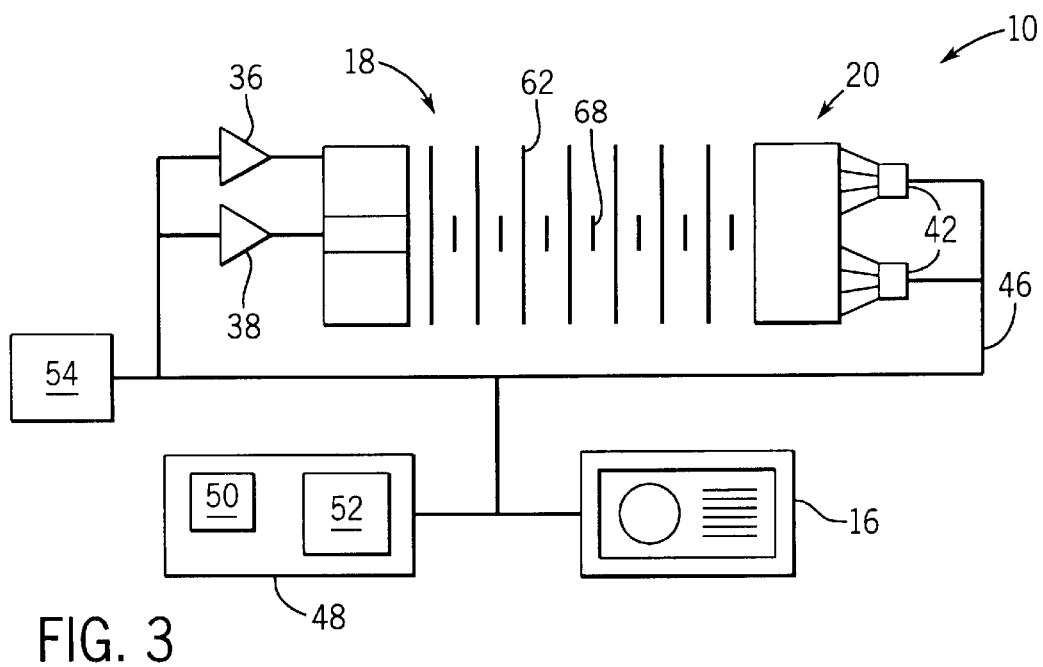
FIG. 3 is a schematic representation of the densitometer of FIG. 1 showing the control of the transmitter unit and the receiver unit by a microprocessor which also controls mechanical subsystems and a display.

Referring now to FIG. 3, the imaging/quantitative ultrasonic device 10 provides an internal bus 46 allowing a computer 48 having a processor 50 and memory 52 to communicate both with the transmitter unit 18 and the receiver unit 20. In this way, the transmitted wave may be controlled according to a program held in memory 52 and the received wave may be processed according to the program in memory 52. The bus 46 also communicates with the display/touch panel 16 which allows inputting of data to the computer 48 and outputting data from the computer 48 during execution of the program 52. The bus 46 also allows communication between the computer 48 and the mechanical subsystems 54 such as pumps for inflating the bladders 34 prior to use or deflating the bladders 34 for storage.

Figure 4:
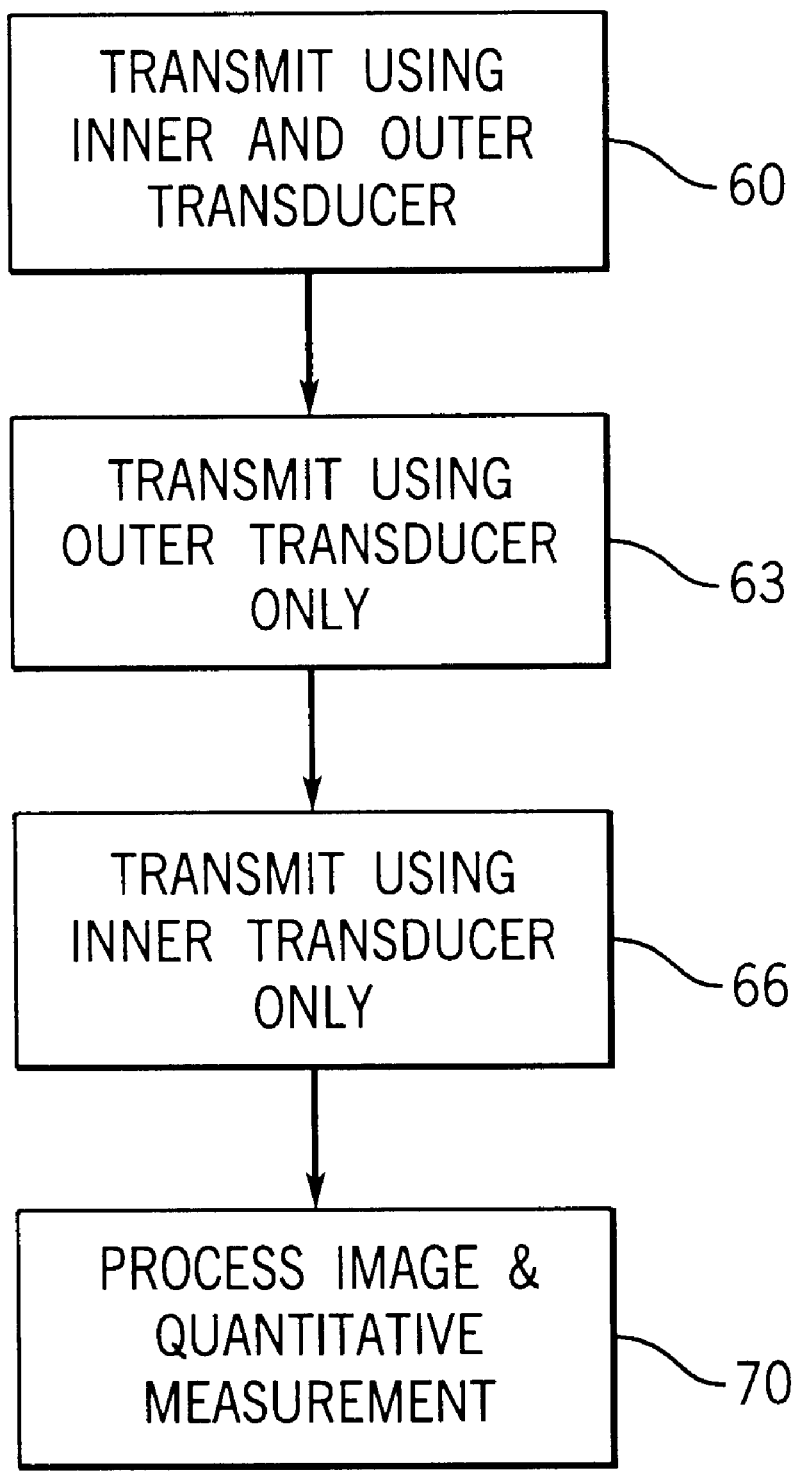
FIG. 4 is a flow chart showing operation of the present invention in obtaining quantitative and image data.

Referring now to FIG. 4, during operation of the program held in memory 52, at a first step indicated by process block 60, the computer 48 energizes both buffer amplifiers 36 and 38 (or switches one buffer to connect with both the ultrasonic elements 24 and 26) to operate ultrasonic elements 24 and 26 in tandem to produce a generally planar wave 62 (shown in FIGS. 3 and 5) generally for imaging purposes.

Referring still to FIG. 4, at optional process block 63, the computer 48 switches the buffer amplifier 38 off (or switches a single buffer amplifier to connect only to the outer ultrasonic element 26) to energize only the outer ultrasonic element 26 for the purpose of creating an outer wave passing largely around the os calcis, as indicated by wave 62. At this time, only outer reception elements 40" of the receiver unit 20 (shown in FIG. 5) are scanned or simultaneously connected together to detect the outer wave 62 and make the necessary measurement typically by combining and averaging of their measured values.

Referring still to FIG. 4, at process block 66, the computer 48 switches the buffer amplifier 36 off (or switches a single buffer amplifier to connect only to the center ultrasonic element 24) to energize only the center ultrasonic element 24 for the purpose of creating a central wave passing through the os calcis, as indicated by wave 68. At this time, only central reception elements 40' of the receiver unit 20 (shown in FIG. 5) are scanned or simultaneously connected together to detect the central wave 68 and make the necessary measurement typically by combining and averaging of their measured values.

At process block 66, the computer 48 processes the image and quantitative data. This image data may consist of amplitude data or attenuation data such as broadband ultrasonic attenuation (BUA) or speed of sound measurements (SOS), some other acoustic parameter(s), or a combination of any or all mapped to a gray scale (or color) value and a spatial location in the image corresponding to the location of each element(s) 40 in the ultrasonic receiver unit 20. The image may be displayed on the display/touch panel 16, and adjustment to the foot position is made, as is described below, and the process repeated as necessary.

In a first embodiment, the image is generated solely from the data collected at process block 60 and quantitative measurements made solely from the data collected at process block 66.

In an alternative embodiment, the data collected at process block 63 may be obtained and used to make a measurement of the scatter ultrasonic energy to refine the quantitative measurements or to image certain structures. Further, the inner ultrasonic element 24 may be used alone for imaging purposes, for example, imaging of the center of the os calcis. Thus generally the invention contemplates obtaining up to three sets of data, data from the inner ultrasonic element 24 alone, data from the outer ultrasonic element 26 alone, and data from both elements, to generate separate image and quantitative information, through combinations of the above.

The precise location of the central reception elements 40' our outer reception elements 40" may be determined automatically from the developed image of process block 63 by techniques known in the art or may be selected manually from the image by the operator. Thus, the reception pattern may be moved depending on the image so that quantitative measurements are made on the correct region. Alternatively, the operator may move the patient's foot, based on the image, to align the appropriate region of the foot with the central reception elements 40' and/or the center ultrasonic element 24. Movement of the foot may be accomplished through the use of a set of shims 17 of predetermined thickness (shown in FIG. 1) fitting into the footwell 14 or by means of a motorized stage supporting the foot but movable by the operator or automatically based on the image. The collected data is processed by the computer 48 using well known techniques, as indicated by process block 70, to produce a quantitative value output to the display/touch screen 16.

Referring now to FIG. 5, although the applicants do not wish to be bound by a particular theory, it is believed that during the generation of the planar wave 62, scatter or refraction occurring along line 72 causes acoustic energy not passing through a central trabecular region 74 of the os calcis 76 of the human heel 78 to be nevertheless diverted to central reception elements 40' and incorporated into the quantitative measurement. Accordingly, by deactivating the annular, outer ultrasonic element 26 during the quantitative portion of the measurement, this scatter along lines 72 may be reduced in favor of a direct path 80 proceeding from center ultrasonic element 24 through the trabecular region 74 of the os calcis 76 to the central receiving elements 40'.

The present invention provides a simple method of reducing this scatter which may be used alone or in combination with synthetic aperture-type techniques in which the phase of ultrasonic signals received by the elements 40 is used to focus the receiver unit 20 on particular regions of the bone of the os calcis 76.

It is specifically intended that the present invention not be limited to the embodiments and illustrations contained herein, but that modified forms of those embodiments including portions of the embodiments and combinations of elements of different embodiments also be included as come within the scope of the following claims. For example, the transmitter unit 18 need not be divided into coaxial regions but may provide for any two independently excitable regions that may be used to develop different data for imaging and quantitative measurement.

What is claimed is:

1. A bone imaging and quantitative ultrasound device comprising:

an ultrasonic receiver unit providing a reception element of a first predetermined area;

an ultrasonic transmitter unit having a transmission element of a second predetermined area, the ultrasonic transmitter unit positioned in opposition across a measurement region from the ultrasonic receiver unit for directing ultrasonic acoustic waves to the reception element, the ultrasonic transmitter unit further including means for independently transmitting ultrasonic acoustic waves from a first and second portion of the transmission element; and a controller communicating with the ultrasonic transmitter unit to alternately transmit ultrasonic acoustic waves from (a) only the first portion of the transmission element for preparing a quantitative data, and (b) both the first and second portions of the transmission element for preparing an image data.

2. The bone imaging quantitative ultrasound device of claim 1 wherein the image data is prepared from the acoustic waves collected by the ultrasonic receiver unit during the transmission from both the first and second portions of the transmission element and the quantitative data is obtained from the acoustic waves collected by the ultrasonic receiver unit during the transmission from only the first transmission element.

3. The bone imaging quantitative ultrasound device of claim 1 wherein the image data is prepared from the acoustic waves collected by the ultrasonic receiver unit during the simultaneous transmission from both the first and second portions of the transmission element and during the transmission from only the first portion of the transmission element, and the quantitative data is obtained from the acoustic waves collected by the ultrasonic receiver unit during the transmission from only the first transmission element.

4. The bone imaging quantitative ultrasound device of claim 1 wherein the image data is prepared from the acoustic waves collected by the ultrasonic receiver unit bone quality measurement to the display from data collected during the reception of ultrasonic acoustic waves from only the first portion of the reception element.

5. The bone imaging quantitative ultrasound device of claim 1 wherein the ultrasonic transmitter unit has a circular transmission element and wherein the means for alternately transmitting ultrasonic acoustic waves from the first and the second portion of the transmission element is an electrically separate circular transducer and a co-axial annular transducer.

6. The bone imaging quantitative ultrasound device of claim 5 wherein the circular transducer has a diameter substantially equal to one inch.

7. The bone imaging quantitative ultrasound device of claim 1 wherein the ultrasonic receiver unit includes an array of receiving elements.

8. The bone imaging quantitative ultrasound device of claim 1 wherein the controller communicates with the ultrasonic receiver unit to sequentially or in combination (a) detect ultrasonic acoustic waves from only a first portion of the reception element when ultrasonic acoustic waves are being transmitted from only the first portion of the transmission element, and (b) detect ultrasonic acoustic waves from both a first and the second portion of the reception element when ultrasonic acoustic waves are being transmitted from both the first and second portions of the transmission element.

9. The bone imaging quantitative ultrasound device of claim 8 including further a display and wherein the controller executes a stored program to output an image to the display from data collected during the reception of ultrasonic acoustic waves from both the first and second portion of the reception element and to output a quantitative bone quality measurement to the display from data collected during the reception of ultrasonic acoustic waves from only the first portion of the reception element.

10. The bone imaging quantitative ultrasound device of claim 1 wherein the transmission element is substantially equal to the reception element.

11. The method recited in claim 10 wherein the ultrasonic transmitter unit has a circular transmission element and wherein the means for alternately transmitting ultrasonic acoustic waves from the first and the second portion of the transmission element is an electrically separate circular transducer and a co-axial annular transducer.

12. The bone imaging quantitative ultrasound device of claim 1 wherein the ultrasonic transmitter unit and the ultrasonic receiver unit are separated by a distance less than twice the diameter of the reception and transmission elements.

13. The bone imaging quantitative ultrasound device of claim 1 further including a foot support in the measurement region to position an os calcis of a human foot substantially along an axis between the ultrasonic transmitter unit and ultrasonic receiver unit aligned with the center of the transmission element.

14. The bone imaging quantitative ultrasound device of claim 1 wherein the foot support includes a positioning means for moving the human foot across the axis between the ultrasonic transmitter unit and ultrasonic receiver unit.

15. A method of providing quantitative and image data of in vivo bone comprising the steps of:
(a) arranging an ultrasonic receiver unit providing a reception element of a first predetermined area in opposition to an ultrasonic transmitter unit having a transmission element of a second predetermined area across a measurement region wherein the ultrasonic transmitter unit including means for independently transmitting ultrasonic acoustic waves from a first and a second portion of the transmission element;
(b) alternately transmitting ultrasonic acoustic waves from (a) only the first portion of the transmission element for preparing a quantitative measurement and (b) both the first and second portions of the transmission element for preparing an image.

16. The method recited in claim 15 wherein the circular transducer has a diameter substantially equal to one inch.

17. The method recited in claim 15 wherein the ultrasonic receiver unit includes an array of receiving elements.

18. The method recited in claim 15 further including the steps of (a) detecting ultrasonic acoustic waves from only a first portion of the reception element when ultrasonic acoustic waves are being transmitted from only the first portion of the transmission element and (b) detecting ultrasonic acoustic waves from both the first portion and a second portion of the reception element when ultrasonic acoustic waves are being transmitted from both the first and second portions of the transmission element.

19. The bone imaging quantitative ultrasound device of claim 18 including further a display and the steps of outputting an image to the display from data collected during the reception of ultrasonic acoustic waves from both the first and second portion of the reception element and outputting a quantitative bone quality measurement to the display from data collected during the reception of ultrasonic acoustic waves from only the center of the reception element.

20. The method recited in claim 15 wherein the transmission element is substantially equal to the reception element.

21. The method recited in claim 15 wherein the ultrasonic transmitter unit and the ultrasonic receiver unit are separated by a distance less than twice the diameter of the reception and transmission elements.

22. The method recited in claim 15 further including the step of positioning an os calcis of a human substantially along an axis between the ultrasonic transmitter unit and ultrasonic receiver unit aligned with the center of the transmission element.

* * * * *

UNITED STATES PATENT AND TRADEMARK OFFICE
CERTIFICATE OF CORRECTION

PATENT NO. : 6,641,537 B2  
APPLICATION NO. : 09/910326  
DATED : November 4, 2003  
INVENTOR(S) : Richard Franklin Morris et al.

Page 1 of 1

It is certified that error appears in the above-identified patent and that said Letters Patent is hereby corrected as shown below:

Col. 6, claims 2-9 and Col. 7, claims 10-14: line 1 of each claim

"imaging quantitative" should be --imaging and quantitative--

Col. 6, line 33 after "unit" insert the following  
--during the transmission from both the first and second portions of the transmission element and the quantitative data is obtained from the acoustic waves collected by the ultrasonic receiver unit during the transmission from only the first transmission element and during the transmission from only the second transmission element.--

Column 8, Line 17 (claim 19):

"The bone imaging quantitative ultrasound device of" should be --The method recited in--.

Signed and Sealed this

Thirtieth Day of January, 2007

JON W. DUDAS  
*Director of the United States Patent and Trademark Office*